United States Patent
Storm

(10) Patent No.: US 7,991,462 B2
(45) Date of Patent: Aug. 2, 2011

(54) METHOD AND APPARATUS FOR MONITORING A SEDATED PATIENT

(75) Inventor: Hanne Storm, Oslo (NO)

(73) Assignee: Med Storm Innovation AS, Oslo (NO)

( * ) Notice: Subject to any disclaimer, the term of this patent is extended or adjusted under 35 U.S.C. 154(b) by 875 days.

(21) Appl. No.: 11/815,213

(22) PCT Filed: Feb. 3, 2006

(86) PCT No.: PCT/NO2006/000049
§ 371 (c)(1),
(2), (4) Date: Aug. 29, 2007

(87) PCT Pub. No.: WO2006/083178
PCT Pub. Date: Aug. 20, 2006

(65) Prior Publication Data
US 2008/0319337 A1    Dec. 25, 2008

(30) Foreign Application Priority Data
Feb. 4, 2005  (NO) .................................. 20050630

(51) Int. Cl.
*A61B 5/00* (2006.01)
*A61B 5/04* (2006.01)
*A61B 5/05* (2006.01)

(52) U.S. Cl. ......... 600/547; 600/300; 600/306; 600/544
(58) Field of Classification Search .................. 600/306, 600/547, 554
See application file for complete search history.

(56) References Cited

U.S. PATENT DOCUMENTS

| 4,291,708 | A | * | 9/1981 | Frei et al. ..................... 600/547 |
| 4,697,599 | A | * | 10/1987 | Woodley et al. ............... 600/547 |
| 4,844,091 | A | * | 7/1989 | Bellak ........................... 600/557 |
| 5,897,505 | A | * | 4/1999 | Feinberg et al. ............... 600/547 |
| 6,117,075 | A | * | 9/2000 | Barnea .......................... 600/300 |

(Continued)

FOREIGN PATENT DOCUMENTS

| WO | 00/72751 | 12/2000 |
| WO | 03/094726 | 11/2003 |
| WO | 2005/117699 | 12/2005 |

OTHER PUBLICATIONS

Storm et al, "Skin conductance with perioperative stress", Acta Anaesthesiologioca Scandinavia, 2002:46:887-895.

*Primary Examiner* — Max Hindenburg
*Assistant Examiner* — Sean P Dougherty
(74) *Attorney, Agent, or Firm* — Christian D. Abel

(57) ABSTRACT

A method and an apparatus for monitoring a sedated patient, the method comprising the steps of providing a skin conductance signal measured at an area of the patient's skin through a time interval, establishing the existence of at least two fluctuation peaks in the skin conductance signal through said time interval, considering if the amplitudes of fluctuation peaks in the skin conductance signal through said interval, the basal level of the skin conductance signal through said interval and the width of the fluctuation peaks in the skin conductance signal fulfils a predetermined criterion, activating a first output signal which indicates the state of awakening in the patient if said criterion is fulfilled, and activating a second output signal which indicates the state of pain in the patient if said criterion is not fulfilled.

16 Claims, 2 Drawing Sheets

U.S. PATENT DOCUMENTS

| | | | |
|---|---|---|---|
| 6,146,334 A * | 11/2000 | Laserow | 600/552 |
| 6,347,238 B1 * | 2/2002 | Levengood et al. | 600/372 |
| 6,751,499 B2 * | 6/2004 | Lange et al. | 600/544 |
| 6,757,558 B2 * | 6/2004 | Lange et al. | 600/544 |
| 7,215,994 B2 * | 5/2007 | Huiku | 600/544 |
| 7,407,485 B2 * | 8/2008 | Huiku | 600/300 |
| 7,580,743 B2 * | 8/2009 | Bourlion et al. | 600/547 |
| 2004/0193068 A1 * | 9/2004 | Burton et al. | 600/544 |

* cited by examiner ical field
METHOD AND APPARATUS FOR MONITORING A SEDATED PATIENT

TECHNICAL FIELD

The invention relates in general to medical technology, and in particular to a method and an apparatus for monitoring patients during surgery and general anaesthesia.

BACKGROUND OF THE INVENTION

During surgery it is very important to observe the patient's level of consciousness and awareness. Few reliable methods of observation exist today. In the field of medical technology there is a problem in producing physical measurements representing the activity in an individual's autonomous nervous system, i.e. in the part of the nervous system, which is beyond the control of the will.

Particularly, there is a special need to monitor the autonomous nervous system of a sedated, non-verbal patient, e.g. a patient in anaesthesia or an artificially ventilated patient, in order to detect if the patient needs more hypnotics because of awakening stimuli or more analgesia because of pain stimuli.

Tests have shown that the skin's conductance changes as a time variable signal which, in addition to a basal, slowly varying value (the so-called basal level or the average conductance level through a certain interval), also has a component consisting of spontaneous waves or fluctuations.

RELATED BACKGROUND ART

WO-03/94726 discloses a method and an apparatus for monitoring the autonomous nervous system of a sedated patient. In the method, a skin conductance signal is measured at an area of the patient's skin. Certain characteristics, including the average value of the skin conductance signal through a time interval and the number of fluctuation peaks through the interval, is calculated. Based on these characteristics, two output signals are established, indicating pain discomfort and awakening in the patient, respectively. The awakening signal is established based on the number of fluctuations and the average value through an interval.

SUMMARY OF THE INVENTION

An object of the present invention is to provide a method and an apparatus for monitoring a sedated patient, which indicates a state of pain/discomfort in the patient and which also provides an indication of awakening of the patient.

Another object of the invention is to provide such a method and apparatus, which relies on the measurement of skin conductance variations due to emotional sweating.

Still another object of the invention is to provide such a method and apparatus, which provides reliable output indications.

A further object of the invention is to provide such a method and apparatus which overcomes disadvantages of the related prior art.

Still another object of the invention is to provide such a method and apparatus, which substantially differ from the related prior art.

According to the invention, the above objects are achieved by a method and an apparatus as defined in the appended claims.

Further advantages and characteristics of the invention are indicated in the dependent claims.

BRIEF DESCRIPTION OF THE DRAWINGS

The invention will be described by example with reference to the drawings, wherein.

DETAILED DESCRIPTION OF THE INVENTION

Figure 1:
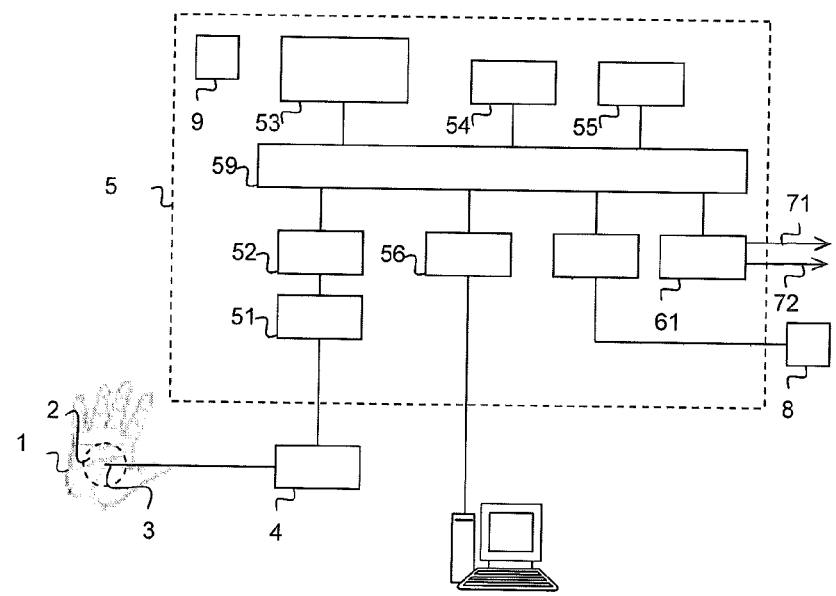
FIG. 1 is a block diagram illustrating a preferred embodiment of an apparatus according to the invention.

FIG. 1 illustrates a block diagram for a preferred embodiment of an apparatus according to the invention. Substantial parts of the apparatus' hardware structure is previously described in the Applicant's related patent application WO-03/94726, with particular reference to the block diagram in FIG. 1 and the corresponding, detailed description. The disclosure of this publication, and the hardware structure and hardware components in particular, is hereby expressly incorporated by reference.

On an area 2 of the skin on a body part 1 of the patient, sensor means 3 are placed for measuring the skin's conductance. The measurement arrangement is disclosed in closer detail in WO-03/94726.

The apparatus comprises a measurement converter 4; which in a preferred embodiment may include a synchronous rectifier and a low pass filter; which converts the measured skin conductance signal into a voltage. This voltage is further sent to control unit 5; which includes time discretization module 51 and analog-digital converter 52, which converts measurement data to digital form. The choice of circuits for time discretization and analog-digital conversion implies technical decisions suitable for a person skilled in the art. In the preferred embodiment, time discretization is done in an integrated circuit, which combines oversampling, filtering and discretization.

In the same way as in the related patent application WO-03/94726, the control unit 5 also includes other data storage 54, 55 and data processing units 53 interconnected to a digital bus 59.

Data processing unit 53 analyses the measured and digitized signal coming from unit 52. The signal is then analysed in order to extract different types of information.

The control unit 5 is arranged to read time-discrete and quantized measurements for the skin conductance from the measurement converter 4, preferably by means of an executable program code, which is stored in the non-volatile memory 54 and which is executed by the processing unit 53. It is further arranged to enable measurements to be stored in the read and write memory 55. By means of the program code, the control unit 5 is further arranged to analyze the measurements in real time, i.e. simultaneously or parallel with the performance of the measurements. The method or process performed by the control unit 5, in order to analyze the skin conductance signal, is distinctive and substantially different from the method/process disclosed in WO-03/94726.

In this context, simultaneously or parallel should be understood to mean simultaneously or parallel for practical purposes, viewed in connection with the time constants which are in the nature of the measurements. This means that input, storage and analysis can be undertaken in separate time intervals, but in this case these time intervals, and the time between them, are so short that the individual actions appear to occur concurrently.

The control unit 5 is further arranged to identify the fluctuations in the time-discrete, quantized measuring signal, by means of a program code portion which is stored in the non-volatile memory 54 and which is executed by the processing unit 53. The program code portion is substantially different from the program code portion disclosed in WO-03/94726.

The control unit 5 is advantageously also arranged to calculate the amplitude of the fluctuation peaks in the time-discrete, quantized measuring signal during a time interval, by means of a program code portion which is stored in the non-volatile memory 54 and which is executed by the processing unit 53.

The processing unit 53, the memories 54, 55, the analog/digital converter 52, the communication port 56, the interface circuit SI and the interface circuit 61 are all connected to a bus unit 59. The detailed construction of such bus architecture for the design of a microprocessor-based instrument is regarded as well-known for a person skilled in the art.

The interface circuit 61 is a digital port circuit, which derives output signals 71, 72 from the processing unit 53 via the bus unit 59 when the interface circuit 61 is addressed by the program code executed by the processing unit 53.

An active state of the first output signal 71 indicates that the analysis of the skin conductance measurement has detected that the patient is receiving awakening stimuli and may need more hypnotics. An active state of the second output signal 72 indicates the state of pain pain/discomfort in the patient.

In a preferred embodiment the display 8 comprises a screen for graphic visualization of the conductance signal, and a digital display for displaying the frequency and amplitude of the measured signal fluctuations. The display units are preferably of a type whose power consumption is low, such as an LCD screen and LCD display. The display means may be separate or integrated in one and the same unit.

The apparatus further comprises a power supply unit 9 for supplying operating power to the various parts of the apparatus. The power supply may be a battery or a mains supply of a known type.

The apparatus may advantageously be adapted to suit the requirements regarding hospital equipment, which ensures patient safety. Such safety requirements are relatively easy to fulfill if the apparatus is battery-operated. If, on the other hand, the apparatus is mains operated, the power supply shall meet special requirements, or requirements are made regarding a galvanic partition between parts of the apparatus (for example, battery operated), which are safe for the patient and parts of the apparatus, which are unsafe for the patient. If the apparatus has to be connected to external equipment, which is mains operated and unsafe for the patient, the connection between the apparatus, which is safe for the patient and the unsafe external equipment requires to be galvanically separated. Galvanic separation of this kind can advantageously be achieved by means of an optical partition. Safety requirements for equipment close to the patient and solutions for fulfilling such requirements in an apparatus like that in the present invention are well-known to those skilled in the art.

Figure 2:
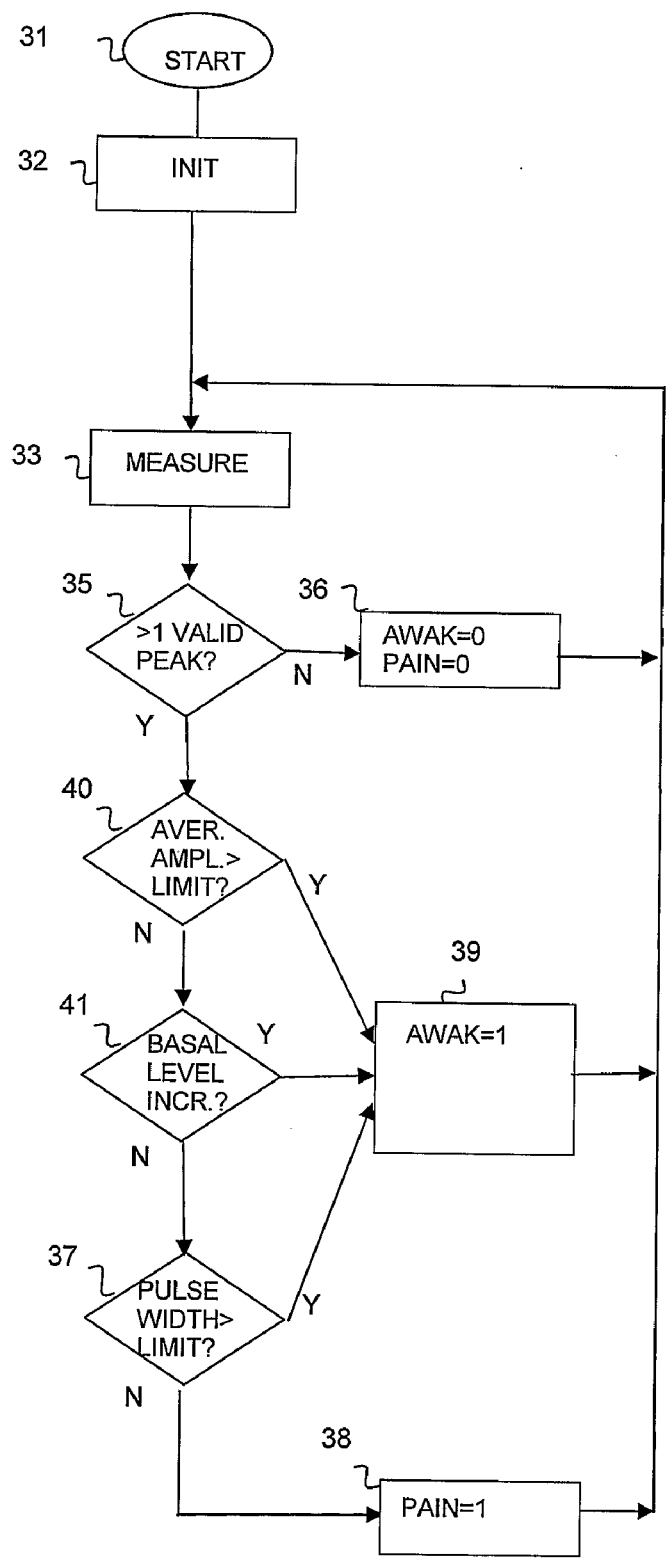
FIG. 2 is a flow chart illustrating a method according to the invention.

FIG. 2 illustrates a flow chart for a method for controlling a warning signal in an apparatus for monitoring the autonomous nervous system of a sedated patient, and especially for detecting stress or discomfort and awakening.

The method starts at reference 31.

The first process step 32 is an initial step, establishing initial values for use in the remaining, repeated process steps.

In step 33, skin conductance signal or EDR (electrodermal response) signal is measured, preferably in microsiemens (uS), time-quantized and converted to digital form using the equipment described with reference to FIG. 1. A time-series of a certain duration, typically between 5 seconds and 40 seconds, and more preferably between 5 and 20 seconds, e.g. about 15 seconds, containing skin conductance data, is acquired during this step. At 15 seconds, with a sampling rate of 20-200 samples per second, the time-series may contain 300-3000 samples.

In the test step 35, a test is performed in order to detect the existence of valid peaks in the time-series of the acquired skin conductance signal. If more than one peak is detected, the process continues at step 40. If one or no peak is detected, the process continues at step 36.

In step 36, both output signals 71 or 72 are set to passive state. Thus, if zero or one valid peak has been detected in step 35, the first output signal 71 indicates no awakening, and the second output signal 72 indicates no pain in the patient.

The existence of a valid peak is established in step 35 if the derivative of the signal changes sign through a small period in the interval. The derivative of the signal is calculated as the difference between two subsequent sample values. In addition, it is possible to use a simple digital filter that needs to see two or more subsequent sign changes before the sign change is accepted.

In the test step 35 it may be necessary to establish additional criteria for when a peak should be considered as valid. In their simplest form such criteria may be based on the fact that the signal amplitude has to exceed an absolute limit in order to be able to be considered a valid fluctuation. A recommended, such reference value for the conductance is between 0.01 $\mu$S and 0.02 $\mu$S, preferably 0.015 $\mu$S.

Alternatively or in addition, it is an advantage to base the criteria on the fact that the signal actually has formed a peak that has lasted a certain time. The criteria may also be based on the fact that the increase in the skin conductance signal value as a function of time must remain below a certain limit, typically 20 $\mu$S/s, if the maximum value is to be considered valid.

Another possible condition for establishing a valid peak is that the absolute value of the change in the conductance signal from a local peak to the following local valley exceeds a predetermined value, such as a value in the range [0.01 uS, 0.02 uS], e.g. 0.015 $\mu$S.

Also, a maximum value appearing at the border of the interval, i.e. the starting point or ending point of the interval should preferably not be regarded as a valid peak.

The object is thereby achieved that artifacts, which can occur in error situations such as, e.g., electrodes working loose from the skin, or other sources of noise or disturbances, does not lead to the erroneously detection of peaks.

Step 40 is a test step wherein the amplitudes of fluctuation peaks in the skin conductance signal through the time interval is considered. An average value of the amplitudes through the interval is calculated. If the calculated average value exceeds a first limit value in the range [0.05 $\mu$S, 0.20 $\mu$S], preferably in the range [0.07 $\mu$S, 0.13 $\mu$S], or more preferably about 0.10 $\mu$S, an awakening state in the patient is detected, and the process continues at step 39.

If the calculated average amplitude value does not exceed the first limit value, the process continues at step 41.

In step 41, the basal level of the skin conductance signal through said interval is considered. If the basal level has shown a recent significant increase, an awakening state in the patient is detected, and the process continues at step 39. More particularly, this is the case if the basal level has increased more than a second limit value in the range [0.05 $\mu$S, 0.3 $\mu$S] during a recently elapsed time interval in the range [10 seconds, 30 seconds]. Preferably, the second limit value is within the range [0.08 $\mu$S, 0.12 $\mu$S] and the recently elapsed time interval is in the range [12 seconds, 18 seconds]. For instance, the second limit value may advantageously be 0.1 µS and the elapsed time interval 15 seconds.

If the basal level has not shown such a significant increase, the process continues at step 37.

In step 37, the width of the pulses of the skin conductance signal is calculated, and the width is compared with a preset reference value. If the pulse width is above the reference value, this indicates that the patient is receiving awakening stimuli and may need more hypnotics, thus the process continues at step 39. If the pulse width is below the second reference value, this indicates a state of pain pain/discomfort. The process continues to step 38, where the output signal 72, indicating pain, is set. The process is then repeated from step 33.

The width of a pulse may be calculated as twice the time difference between the local minimum value and the local peak in one fluctuation The width may also be calculated as the time difference between the local minimum values in the skin conductance signal. The width of a pulse may alternatively be calculated as the time difference between local peaks in the skin conductance signal. When several pulses are detected in the time series, the maximum width may advantageously be stored and used for the further processing. Another way of measuring the width of the pulses is to count the number of pulses during the time interval and calculating the width as the length of the time interval divided by the number of pulses during the time interval. Even another way of measuring the width of the pulses is to ensure that, during the time period, at least more than one pulse has a width above a preset reference value. Then, the average pulse width is calculated, based on the width of the pulses with a width above the preset value.

The reference value of the pulse width should be within the range [1 second, 5 seconds]. In order to obtain even better and more reliable results, the reference value should be within the range [1.5 seconds, 3 seconds], e.g. about 2 seconds.

In step 39, the output signal 71 is set or activated. The process is then repeated from step 33.

The process may be interrupted or terminated by an operating device (not shown) or by a command input from the communication port 56.

An improvement to the method illustrated in FIG. 2 will be described in the following:

In the embodiment in FIG. 2, a time-series is first acquired and subsequently analyzed. As an advantageous alternative, data acquisition and analysis are performed as separate, independent processes, concurrently executed by the processing unit 53.

A data acquisition process is then performed, which virtually continuously updates a portion of the memory 55 with the latest e.g. 15 seconds of skin conductance signal values.

An analysis process is initiated e.g. every 1 second. This process will analyze the latest e.g. 15 seconds of skin conductance data, acquired by the concurrently executed data acquisition process. All the process steps 33-39 are performed by the analysis process, while the initial process step 32 is performed in advance, as initial step.

This solution leads to an even faster and more reliable indication of awakening, compared to the simpler method described with reference to FIG. 2.

The invention has been primarily described with reference to human patients. It should be appreciated that the invention also may be used with animals.

The invention claimed is:

1. Method for monitoring a sedated patient, comprising the following steps, performed by a control unit that includes a processing unit:

providing a skin conductance signal measured at an area of the sedated patient's skin through a time interval, processing the skin conductance signal to establish an existence of at least two fluctuation peaks in the skin conductance signal through said time interval, considering if amplitudes of fluctuation peaks in the skin conductance signal through said interval, basal level of the skin conductance signal through said interval and a width of the fluctuation peaks in the skin conductance signal fulfils the following three predetermined criteria:

if an average of said amplitudes exceeds a first limit value, said first limit value having a range of 0.05 µS to 0.20 µS, if said basal level has shown an increase of more than a second limit value, said second limit value having a range of 0.05 µS to 0.3 µS during a recently elapsed time interval in a range of 10 seconds to 30 seconds, and if said width of the fluctuation peaks exceeds a third limit value, said third limit value having a range of 1 second to 5 seconds, the method further comprising the steps of activating a first output signal which indicates a state of awakening in the sedated patient if one of said criteria is fulfilled, and activating a second output signal which indicates a state of pain in the sedated patient if none of said criteria is fulfilled.

2. Method according to claim 1, wherein said first limit value has a range of 0.07 µS to 0.13 µS.

3. Method according to claim 1, wherein said second limit value has a range of 0.08 µS to 0.12 µS and said recently elapsed time interval is in a range of 12 seconds to 18 seconds.

4. Method according to claim 1, wherein said third limit value has a range of 1.5 seconds to 3 seconds.

5. Method according to claim 1, wherein said step of establishing the existence of at least two fluctuation peaks in the skin conductance signal through said time interval comprises the substep of establishing an existence of a valid peak if a derivative of the skin conductance signal changes sign through a period in the time interval.

6. Method according to claim 5, wherein said derivative is calculated as a difference between two subsequent sample values.

7. Method according to claim 5, wherein an additional criterion is established for when a peak is considered to be a valid peak, including ensuring that an amplitude of the skin conductance signal exceeds an absolute limit value selected from a range of 0.01 uS to 0.02 uS.

8. Method according to claim 5, wherein an additional criterion is established for when a peak is considered to be a valid peak, including ensuring that an increase in the skin conductance signal as a function of time remains below a certain limit.

9. Method according to claim 5, wherein an additional criterion is established for when a peak is considered to be a valid peak, including ensuring that an absolute value of a change in the conductance signal from a local peak to a following local valley exceeds a predetermined value selected from a range of 0.01 uS to 0.02 uS.

10. Method according to claim 5, wherein an additional criterion is established for when a peak is considered to be a valid peak, including ensuring that a starting point or an ending point of the time interval is not regarded as a valid peak.

11. Method according to claim 1, wherein a value of the width of a fluctuation peak is provided by calculating twice a difference from a local minimum point to a local peak in the skin conductance signal.

12. Method according to claim 1, wherein said step of providing a width value comprises calculating a time difference between local minimum points or between local peaks in the skin conductance signal.

13. Method according to claim 1, wherein said step of providing a width value comprises counting a number of pulses during the time interval and calculating the width as a length of the time interval divided by said number of pulses.

14. Method according to claim 1, wherein data acquisition and data analysis are performed sequentially by said processing unit.

15. Method according to claim 1, wherein data acquisition and data analysis are performed concurrently by said processing unit.

16. Apparatus for monitoring a sedated patient, comprising
measurement equipment for providing a skin conductance signal measured at an area of the sedated patient's skin through a time interval, and
a control unit, including a processing unit which is arranged to perform the following steps:
processing the skin conductance signal to establish an existence of at least two fluctuation peaks in the skin conductance signal through said time interval,
considering if amplitudes of fluctuation peaks in the skin conductance signal through said interval, basal level of the skin conductance signal through said interval and a width of the fluctuation peaks in the skin conductance signal fulfils the following three predetermined criteria:
if an average of said amplitudes exceeds a first limit value in the range of 0.05 µS to 0.20 µS,
if said basal level has shown an increase of more than a second limit value in a the range of 0.05 µS to 0.3 µS during a recently elapsed time interval in the range of 10 seconds to 30 seconds, and
if said width of the fluctuation peaks exceeds a third limit value of 1 second to 5 seconds,
the processing unit being further arranged to
activating a first output signal which indicates a state of awakening in the sedated patient if one of said criteria is fulfilled, and
activating a second output signal which indicates a state of pain in the sedated patient if none of said criteria is fulfilled.

\* \* \* \* \*